United States Patent
Zeitlin et al.

(10) Patent No.: US 6,528,530 B2
(45) Date of Patent: *Mar. 4, 2003

(54) PHENIDATE DRUG FORMULATIONS HAVING DIMINISHED ABUSE POTENTIAL

(75) Inventors: Andrew L. Zeitlin, Millington, NJ (US); Maghsoud M. Dariani, Fanwood, NJ (US)

(73) Assignee: Celgene Corporation, Warren, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/955,556

(22) Filed: Sep. 18, 2001

(65) Prior Publication Data

US 2002/0035126 A1 Mar. 21, 2002

Related U.S. Application Data

(63) Continuation of application No. 09/318,151, filed on May 25, 1999, now Pat. No. 6,355,656, which is a continuation-in-part of application No. 08/827,230, filed on Apr. 2, 1997, now Pat. No. 5,908,850, which is a continuation of application No. 08/567,131, filed on Dec. 4, 1995, now abandoned.

(51) Int. Cl.$^7$ ............................................. A61K 31/445
(52) U.S. Cl. ........................................................ 514/317
(58) Field of Search ........................................ 514/317

(56) References Cited

U.S. PATENT DOCUMENTS

| | | | |
|---|---|---|---|
| 2,507,631 A | 5/1950 | Hartmann et al. ........... 260/294 |
| 2,957,880 A | 10/1960 | Rometsch .................... 546/233 |
| 4,992,445 A | 2/1991 | Lawter et al. ............... 514/279 |
| 5,104,899 A | 4/1992 | Young et al. ................ 514/646 |
| 5,114,946 A | 5/1992 | Lawter et al. ............... 514/279 |
| 5,217,718 A | 6/1993 | Colley et al. ................ 424/449 |
| 5,283,193 A | 2/1994 | Yamamoto et al. ......... 435/280 |
| 5,284,769 A | 2/1994 | Evans et al. ................. 435/280 |
| 5,331,000 A | 7/1994 | Young et al. ................ 514/570 |
| 5,362,755 A | 11/1994 | Barberich et al. ........... 514/649 |
| 5,375,693 A | 12/1994 | Woosley et al. ............. 514/317 |
| 5,449,743 A | 9/1995 | Hartmann et al. ........... 528/355 |
| 5,773,478 A | 6/1998 | Richards et al. ............ 514/649 |
| 5,837,284 A | 11/1998 | Mehta et al. ................ 424/456 |
| 5,874,090 A | 2/1999 | Baker et al. ................. 424/600 |
| 5,908,850 A | 6/1999 | Zeitlin et al. ................ 514/315 |
| 6,255,325 B1 * | 7/2001 | Dariani et al. .............. 514/317 |

FOREIGN PATENT DOCUMENTS

| | | |
|---|---|---|
| WO | WO 97/03671 | 2/1997 |
| WO | WO 97/03672 | 2/1997 |
| WO | WO 97/03673 | 2/1997 |
| WO | WO 99/03471 | 1/1999 |

OTHER PUBLICATIONS

Angrist et al., *J. Clin. Psychopharma.*, 1992, 12, 268–272.
Barkley et al., *Pediatrics*, 1990, 86, 184–192.
Barkley et al., *Pediatrics*, 1991, 87, 519–531.
Golinko, *Prog. Neuro–Psychopharmacol. & Biol. Phsychiat.*, 1984, 8, 1–8.
Aoyama et al., "Pharmacolinetics and pharmacodynamics of (+)–threo–methylphenidate enantiomer in patients with hypersomnia", *Clin. Pharmacol. Ther.*, 1994, 55(3), 270–276.
Bowden et al., "Reactions of Carbonyl Compounds in Basic Solutions the Alkaline Hydrolysis of N–Methyl, N–Phenyl, and Bicyclo Lactams Penicillins, and N–Alkyl–N–methylacetamides", *J. Chem. Soc. Perkin Trans.*, 1990, 12, 2111–2116.
Brown, "Pharmacological Action and Drug Development", *Chirality in Drug Design and Synthesis*, Academic Press Inc., 1990, 4–7.
Brown G., "The Use of Methylphenidate for Cognitive Decline Associated with HIV Disease", *Int'l J. Psychiatry Med.*, 1995, 25(1), 21–37.
Corey et al., "A New Synthetic Approach to the Penicillins", *J. Am. Chem. Soc.*, 1965, 87(11), 2518–2519.
Ding et al., "Cis– and trans–Axetidin–2–ones from Nitrones and Copper Acetylide", *J. Chem. Soc. Perkin*, 1976, 22, 2382–2386.
Douzenis et al., "Phychiatric Disorder in HIV Disease: Description of 200 Referrals to a Liaison psychiatry Service", *Proc. 7th. Int'l Conf. AIDS*, 1991, 215 (M.B.2135—Summary).
Earle et al., "Synthesis and Hydrolysis of some Fused–ring β–Lactams", *J. Chem. Soc.*, 1969, 2093–2098.
Greenhill L., "Attention–Deficit Hyperactivity Disorder", *Child & Adol. Psych. Clin. N.A.*, 1995, 4(1), 123–168.
Greenhill, "Pharmacologic Treatment of Attention Deficit Hyperactivity Disorder", *Pediatric Psychopharmacology*, 1992, 15(1), 1–27.
Holmes et al., "Psychostimulant Response in Aids–Related Complex Patients", *J. Clin. Psychiatry*, 1989, 50(1), 5–8 (Biosis Abstract No. 87129969).
Klibanov, "Asymmetric Transformations Catalyzed by Enzymes in Organic Solvents", *Acc. Chem. Res.*, 1990, 23, 114–120.
Moll F., "Darstellung von 1–Aza–bicyclo[4.2.0]octan–2–on", *Naturforsch Teil B.*, 1966, 21, 297.
Navia et al., "The AIDS Dementia Complex: I. Clinical Features", *Annals of Neurology*, 1986, 19, 517–524.
Patrick et al., "Pharmacology of the Enantiomers of threo–Methylphenidate", *J. Pharmacol & Exp. Terhap.*, 1987, 241, 152–158.

(List continued on next page.)

Primary Examiner—Raymond Henley, III
(74) Attorney, Agent, or Firm—Woodcock Washburn LLP

(57) ABSTRACT

Phenidate drug formulations are provided having reduced potential for drug abuse. Dosage forms for treating Attention Deficit Disorder, Attention Deficit Hyperactivity Disorder, AIDS Dementia Complex and cognitive decline in HIV-AIDS are provided which minimize drug hypersensitivity, toxicity, side effects, euphoric effect, and drug abuse potential. Such dosage forms comprise D-threo stereoisomer of a phenidate in the substantial absence of all other stereoisomers.

4 Claims, No Drawings

OTHER PUBLICATIONS

Rieder et al., "Diagnosis of Sulfonamide Hypersensitivity Reactions by In–Vitro "Rechallenge" with Hydroxylamine Metabolites", *Ann. Intern. Med.*, 1989, 110, 286–289.

Scott, "Stereoisomers and Drug Toxicity", *Drug Safety*, 1993, 8(2), 149–159.

Srinivas et al., "Enantioselective Pharmacokinetics of dl–threo–Methylphenidate in Humans", *Pharmacol Res.*, 1993, 10(1), 14–21.

Srinivas et al., "Enantioselective Pharmacolinetics and Pharmacodynamics of Racemic Threo–Methylphenidate in Children with Deficit Hyperactivity Disorder", *Clin. Pharmacol.*, 1992, 52(5), 561–568 (Biosis Abstract No. 95066168).

Srinivas et al., "Enantiomeric Gas Chromatography Assay with Electron Capture Detection for d–Ritalinic Acid in Plasma", *J. Chromatagraph*, 1990, 530, 327–336.

Srinivas et al., "Sterioselective Disposition of Methylphenidate in Children with Attention Deficit Disorder", *J. Pharmacol. Exp. Ther.*, 1987, 241(1), 300–306.

Staal et al., "Glutathione deficiency and human immunodeficiency virus infection", *Lancet*, 1992, 339, 909–912.

Uetrecht et al., "Idiosyncratic Drug Reactions: Possible Role of Reactive Metabolites Generated by Leukocytes", *Pharmacol Res.*, 1989, 6(4), 265–273.

White et al., "Methylphenidate as a Treatment for Depression in Acquired Immunodeficiency Syndrome: An n–of–1 Trial", *J. Clin. Psychiatry*, 1992, 53(5), 153–156.

* cited by examiner

PHENIDATE DRUG FORMULATIONS HAVING DIMINISHED ABUSE POTENTIAL

This application is a continuation of U.S. application Ser. No. 09/318,151 filed May 25, 1999, now U.S. Pat. No. 6,355,656 which is a CIP of U.S. application Ser. No. 08/827,230 filed Apr. 2, 1997, now U.S. Pat. No. 5,908,850, which is a continuation of U.S. application Ser. No. 08/567,131 filed Dec. 4, 1995, now abandoned the contents of which are incorporated herein in their entirety.

FIELD OF THE INVENTION

The present invention relates to phenidate drug compositions for treating certain Central Nervous System disorders such as Attention Deficit Disorder (ADD), Attention Deficit Hyperactivity Disorder (ADHD), HIV/AIDS cognitive decline, and AIDS Dementia Complex. This invention features such drugs having decreased side effects, reduced euphoric effect, and reduced drug abuse potential.

BACKGROUND OF THE INVENTION

Attention Deficit Disorder (ADD) is the most commonly diagnosed nervous system illness in children. Patrick et al., J. Phamacol. & Exp. Therap., 241:152–158 (1987). Symptoms of ADD include distractibility and impulsivity. A related disorder, termed Attention Deficit Hyperactivity Disorder (ADHD), is further characterized by increased symptoms of hyperactivity in patients. Racemic methylphenidate (e.g., Ritalin® ) is a mild Central Nervcus System stimulant with pharmacological activity qualitatively similar to amphetamines, and has long been the drug of choice for symptomatic treatment of ADD in children. Graenhill, L., Child & Adol. Psych. Clin. N.A., Vol. 4, Number 1:123–165 (1995).

Current administration of racemic methylphenidate, however, often results in notable aide effects such as anorexia, weight loss, insomnia, dizziness and dysphoria. Additionally, racemic methylphenidate, which is a Schedule II controlled substance, produces a euphoric effect when administered intravenously or through inhalation, and thus carries a high potential for substance abuse in patients.

At least 70% of HIV-infected individuals who have developed Acquired Immunodeficiency Syndrome (AIDS) eventually manifest cognitive defects, and many display signs and symptoms of dementia. See Navia at al., Annals of Neurology, 19:517–524 (1986). Complaints of forgetfulness, loss of concentration, fatigue, depression, loss of attentiveness, mood swings, and thought disturbance are common in patients with Human Immunodeficiency Virus (HIV) disease. Douzenis et al., Proc. 7th int'l. Conf. AIDS, 1, MB, 2135:215 (1991); Holmes et al., J. Clin. Psychiatry, 50:5–8 (1989). Racemic methylphenidate has been used to treat cognitive decline in AIDS/ARC patients. Brown, G., Intl. J. Psych. Med. 25(1): 21–37 (1995). As described above, racemic methylphenidate, a Schedule II controlled substance, produces a euphoric effect when administered intravenously or through inhalation, and thus carries a high potential for drug abuse.

U.S. Pat. No. 2,507,631, to Hartmann et al. describes methylphenidate and processes for making the same. U.S. Pat. No. 2,957,880, to Rometsch et al. describes the conversion of α-aryl-α-piperidyl-(2)-acetic acids and derivatives thereof (including methylphenidate) into their respective racemates. Each of these patents is incorporated herein by reference.

Holmes et al., J. Clin. Psychiatry, 50:5–8 (1989) reported on the use of racemic methylphenidate (Ritalin®) and dextroamphetamines in the treatment of cognitive impairment in AIDS patients.

Srinivas et al., J. Pharmacol. & Exp Therap., 241:300306 (1987) described use of racemic dl-threo-methylphenidate (Ritalin®) in the treatment of ADD in children. This study noted a 5-fold increase in plasma levels of d-threo-methylphenidate in children treated with racemic methylphenidate, but was otherwise inconclusive with regard to the efficacy of a single methylphenidate isomer at therapeutically significant doses.

Srinivas et: al., Clin. Pharmacol. Ther., 52:561–568 (1992) studied the administration of dl-threo, d-threo and l-threo-methylphenidate to children suffering from ADHD. While Srinivas et al. reported the pharmacodynamic activity of dl-threo-methylphenidate resides in the d-threo isomer, this study investigated neither the adverse side effects of the l-threo isomer, nor the euphoric effects of the single isomers or racemate. Single isomer dosages below ½ of the racemate dosage were not studied.

Patrick et al., J. Pharmacol. & Exp. Therap., 241:152158 (1986) examined the pharmacology of the enantiomers of threo-methylphenidate, and assessed the relative contribution of each isomer to central and peripheral actions of Ritalin®.

Brown, G., Intl. J. Psych. Med., 25 (1) :21–37 (1995) reported the use of racemic methylphenidate for the treatment of AIDS' cognitive decline.

Patrick et al., Psychopharmacology: The Third Generation of Progress, Raven Press, N.Y. (1987) examined the pharmacokinetics and actions of methylphenidate in the treatment of Attention Deficit Hyperactivity Disorder (ADHD). Patrick noted the d-threo isomer possesses higher activity than the l-threo isomer, and that d-threo methylphenidate may be responsible for the therapeutic activity in the racemic drug.

Aoyama et al., Clin. Pharmacol. Ther., 55:270–276 (1994) reported on the use of (+)-threo-methylphenidate in the treatment of hypersomnia. Aoyama et al. describe a correlation between sleep latency in patients and plasma concentration of (+)-threo-methylphenidate.

Glutathione is an important antioxidative agent that protects the body against electrophilic reactive compounds and intracellular oxidants. It has been postulated that HIV-AIDS patients suffer from drug hypersensitivity due to drug overload and an acquired glutathione deficiency. See Uetrecht et al., Pharmacol. Res., 6:265–273 (1989). Patients with HIV infection have demonstrated a reduced concentration of glutathione in plasma, cells and broncho-alveolar lavage fluid. Staal et al., Lancet, 339:909–912 (1992). Clinical data suggests that HIV-seropositive individuals display adverse reactions to the simultaneous administration of several otherwise therapeutic drugs. Rieder et al., Ann. Intern. Med., 110:286–289 (1989). It is desirable to provide for the administration of methylphenidate in reduced dosages among patients with drug hypersensitivity due to HIV infection.

There is a long-felt and very intense need for phenidate drug compositions, especially methyl phenidate, which are less susceptible to unlawful abuse and which exhibit diminished side effects while retaining therapeutic efficacy.

SUMMARY OF INVENTION

Phenidate drugs in accordance with this invention have the structure:

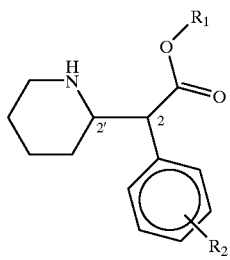

where $R_1$ is $C_1$–$C_4$ alkyl and $R_2$ is either $C_1$–$C_4$ alkyl or hydrogen. Of this family of drugs, methylphenidate, where $R_1$ is methyl and $R_2$ is hydrogen, is the most well known, having long been prescribed under the trade mark Ritalin®. Phenidate drugs are α-aryl-α-piperidyl-2-acetic acids and comprise two centers of asymmetry, existing as four separate optical isomers as follows:

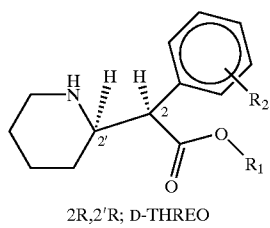
2R,2'R; D-THREO

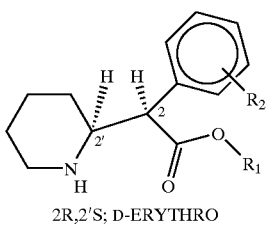
2R,2'S; D-ERYTHRO

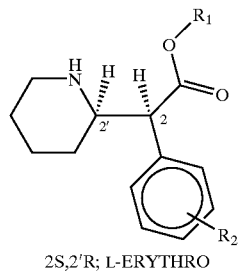
2S,2'R; L-ERYTHRO

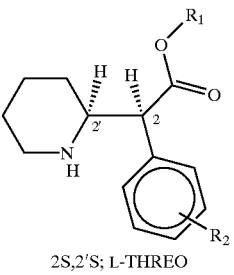
2S,2'S; L-THREO

It is known that certain physiological properties of methylphenidate and other phenidate drugs are dependent upon stereochemistry. Thus, while the threo racemate of methylphenidate is understood to produce the desired central nervous system action, the erythro racemate is thought to contribute to hypertensive side effects.

It is now believed, however, that another stereochemical distinction also applies. Studies in animals, children and adults have demonstrated pharmacological activity in the D-threo isomer of methylphenidate (2R,2'R). See Patrick et al., *J. Pharmacol. & Exp. Therap.*, 241:152–158 (1987). The role of the L-threo isomer in toxicity or adverse side effects has not been examined heretofore although the potential for isomer ballast in methylphenidate and other phenidate drugs is of concern for many patient groups, particularly those drug hypersensitive patients as described above.

Although L-threo-methylphenidate is rapidly and stereoselectively metabolized upon oral administration by extensive first pass metabolism, intravenous administration or inhalation results in high L-threo methylphenidate serum levels. Srinivas et al., *Pharmacol. Res.*, 10:14–21 (1993). Intravenous administration and inhalation are methods of choice by drug abusers of current, racemic methylphenidate formulations. It is now believed that the euphoric effect produced by current formulations of methylphenidate is due to the action of L-threo-methylphenidate, rather than the pharmaceutically efficacious D-threo compound.

Accordingly, it has now been discovered that the incorporation into pharmaceutical formulations of the D-threo isomer (2R,2'R) of a phenidate drug, especially methylphenidate, with the substantial exclusion of the other three isomers of the phenidate, especially the L-threo isomer, produces a phenidate medication dosage form which retains high pharmaceutical efficacy levels upon administration to patients, while simultaneously possessing fewer or reduced side-effects, reduced euphoric effect and reduced potential for abuse.

Patients suffering from Attention Deficit Disorder, Attention Deficit Hyperactivity Disorder, AIDS cognitive decline, and AIDS Dementia Complex are benefitted by receiving phenidate drug, especially the preferred methylphenidate, in a dosage form which substantially excludes three of the four stereoisomers, D erythro, Lerythro, and L-threo. Stated alternatively, such dosage forms comprise D-threo phenidate in the substantial absence of L-threo and both erythro stereoisomers.

The present invention also provides dosage forms of phenidate drugs for treating Attention Deficit Disorder and Attention Deficit Hyperactivity Disorder in children and adults while providing for reduced side effects, reduced euphoric effect and reduced potential for abuse. This is accomplished by formulating dosage forms for administration to patients comprising D-threo-phenidate or a pharmaceutically acceptable salt thereof, substantially free of the L-threo isomer and both erythro isomers. The invention further provides methods of treating AIDS-related dementia and related cognitive disorders while providing for reduced side effects, reduced euphoric effect, and reduced abuse potential comprising administering D-threo-phenidate (2R, 2'R) of the formula:

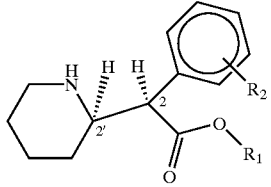

or a pharmaceutically acceptable salt thereof, substantially free of the other three stereoisomeric forms of the drug.

In accordance with the invention, $R_1$ is methyl, ethyl, propyl, isopropyl, n-butyl, isobutyl or tert-butyl. It is preferred that $R_1$ be methyl. $R_2$ may be hydrogen, methyl, ethyl, propyl, isopropyl, n-butyl, isobutyl or tert-butyl and may appear either ortho, meta or para to the acetic acid moiety. Additional substitutients may also appear in the phenidate drug molecule, either in the aryl ring, in the pipiridine heterocycle of in the ester function, however, extensive substitution is not preferred.

Salts of phenidates, such as the conventional hydrochloride salts, are also within the spirit of the invention and all such salts are specifically contemplated hereby.

Preferably, $R_1$ is methyl and $R_2$ is hydrogen such that the phenidate drug is methylphenidate.

Prescription of methylphenidate to treat AIDS cognitive decline and AIDS Dementia Complex associated with HIV infection is becoming increasingly popular. However, high doses in excess of 40 mg/day are not well tolerated by a substantial number of HIV-infected patients when treated over weeks or months. Brown, G., *Int'l J. Psychiatry. Med.*, 25:21–37 (1995). The exclusive D-threo isomer formulations of the present invention enable a lowered dosing therapy with avoidance of the administration of the stereoisomer believed to be responsible for adverse side effects and abuse potential resulting in improved efficacy for diseased patients and particularly HIV-infected patients.

Racemic methylphenidate and its individual isomers are known. See U.S. Pat. Nos. 2,507,631 and 2,957,880. They can be prepared by conventional techniques, and can be obtained from a variety of commercial sources. Moreover, the D-threo-isomer of methylphenidate and other phenidate drugs can be prepared in accordance with Ser. No. 08/583,317 filed Jan. 5, 1996, which application forms a parent to this application and has been incorporated herein by reference. Examples forming part of this application set forth certain preferred synthetic routes to the phenidate compounds useful in the practice of this invention. Persons of ordinary skill will be able to modify such procedures to prepare the lower alkyl substituted phenyl derivatives and lower alkyl esters contemplated herein without undue experimentation. Thus, preparation of ethyl, propyl, isopropyl etc. esters is a simple matter in view of the synthetic schemes set forth. Likewise, substituting the phenyl ring with one or more alkyl or other substituients may also be accomplished.

The dosage forms of the present invention can be administered orally, rectally, parenterally, or transdermally, alone or in combination with other psychostimulants, antidepressants, and the like to a patient in need of treatment. Oral dosage forms include tablets, capsules, dragees, and other conventional, pharmaceutical forms. Isotonic saline solutions, conveniently containing about 1–40 milligrams of drug per milliliter can be used for parenteral administration which includes intramuscular, intrathecal, intravenous and intra-arterial routes. Rectal administration can conveniently be effected through the use of suppositories such as can easily be formulated from conventional carriers such as cocoa butter. Transdermal administration can be effected through the use of transdermal patch delivery systems and the like. The preferred routes of administration are oral and parenteral.

The dosage employed should be carefully titrated to the patient, considering age, weight, severity of the condition, and clinical-profile. Typically, the amount of d-threo-methylphenidate administered will be in the range of 1–50 mg/day, but the actual decision as to dosage will depend upon the exact phenidate drug being employed and will be made by the attending physician as a matter of routine. Such physician can, however, determine an appropriate regime employing well-known medical considerations. Such persons will appreciate that the overall dosage amount will be significantly smaller than that used with the corresponding racemic drug, since the undesired enantiomers are not included in the present dosage forms.

Accordingly, a pharmaceutically effective amount of a phenidate drug in accordance with this invention will be understood by persons of ordinary skill in the art to be that amount of the selected D-threo phenidate which, upon administration to a patient, would result in a sensible and therapeutically useful effect.

When phenidates other than methylphenidate are to be administered, it will be appreciated that the effective amount of drug will likely be different than for methylphenidate. Determination of such amount, however, is well within the routine skill of the practitioner. In accordance with preferred embodiments, from 1 to about 50 mg will be administered to patients, with from about 2 to about 20 mg per day being still more preferred. In still more preferred embodiments, patients will receive from about 2½ to about 12 mg per day.

It is desirable to provide unit dosage forms for administration of compounds of the invention comprising from about 1 to about 50 mg of drug, with amounts of from about 2 to about 20 and particularly from about 2½ to about 12 mg being still more preferred. Oral administration is the protocol of choice, however other routes of administration, such as intravenous, intraperitoneal, rectal and the like may also be employed in formulating the unit dosage forms of this invention. Carriers, diluents and excipients are conventionally employed in formulating unit dosage forms and the same are selected as a matter of routine depending upon the selected route of administration. For oral administration, formulation into tablets using tabletting excipients are conveniently employed, although capsular and other oral forms are also useful.

The present invention provides enhanced relief for patients suffering from Attention Deficit Disorder and Attention Deficit Hyperactivity Disorder while providing for reduced side effects, reduced euphoric effect, and reduced abuse potential through administration of D-threo-methylphenidate substantially free of the L-threo and other isomers. The invention gives rise to methods of treatment of AIDS related dementia and related cognitive disorders with D-threo-methylphenidate substantially free of the remaining isomers.

The term, "substantially free as it applies to a stereoisomer in accordance with a composition of this invention means that the composition contains no more than 10% by weight of the isomer in question. It is preferred that such composition have less than about 2% of the unwanted isomers and even more preferred that less than 1% be present. When applied to a plurality of stereoisomers, then all of the isomers, taken together, comprise no more than 10% by weight of the composition and preferrably less than 2%. It is preferred that compositions characterized as being "substantially free" of all stereoisomers but the D-threo isomer comprise no more than about 5% of other isomers. It is still more preferred that no more than 1% of the undesired isomers be present.

The following examples will serve to further typify the nature of the invention, but should not be construed as a limitation on the scope thereof, which is defined solely by the appended claims.

EXAMPLES

A suitable salt medium for the microbiological transformations described in the following examples has been denominated "media A" and has the following composition:

| | |
|---|---|
| $MgSO_4$ | 1.00 g/L |
| $CaCl_2$ | 0.021 g/L |
| $ZnSO_4 \cdot 7H_2O$ | 0.20 mg/L |
| $MnSO_4 \cdot 4H_2O$ | 0.10 mg/L |
| $H_3BO_3$ | 0.02 mg/L |
| $CUSO_4 \cdot 5H_2O$ | 0.10 mg/L |
| $CoCL_2 \cdot 6H_2O$ | 0.05 mg/L |
| $NiCl_2 \cdot 6H_2O$ | 0.01 mg/L |
| $FeSO_4$ | 1.50 mg/L |
| $NaMoO_4$ | 2.00 mg/L |
| Fe EDTA | 5.00 mg/L |
| $KH_2PO_4$ | 20.00 mg/L |
| NaOH | to pH 7 |

Example 1

Preparation of D-threo-2-(piperid-2-yl)-2-phenyl-acetic acid from trans-7-phenyl-1-azabicyclo(4,2,0)-octan-8-one Preparation of Biocatalyst Lactamase is obtained from *Pseudomonas cepacia* grown on 1–2% penicillin as the sole carbon and nitrogen source in a minimal media. Fifty milliliters of Media A containing 2 g/l of penicillin is inoculated with *Pseudomonas cepacia*. After the mixture is incubated at 30° C. for 48 hours, 10 ml of the mixture are subcultured into 250 ml of Media A with 2 g/l penicillin. After 40 hours of incubation at 30° C., the cells are concentrated to a paste by centrifugation at 10,000 G and washed with 50 ml phosphate buffer pH 7 and again concentrated to a paste by centrifugation at 10,000 G. The washed paste then is passed through a French Press at 17,000 psi to rupture the cells and produce cell extract. Cell debris is removed by centrifugation for one half hour at 100,000 G and the enzyme-containing supernatant collected.

Racemic (+/−)trans-7-phenyl-1-azabicyclo(4,2,0)octan-8-one (0.5 g) is added to a mixture of 20 ml of 50 mM potassium phosphate buffer pH 7 and 1 ml cell extract of lactamase. The reaction is maintained at 30° C. until the enantiomer excess as determined by chiral chromatography is no less than 98% of D-ritalinic acid, generally about 3 hours under these conditions. A lactamase with opposite stereoselectivity obtained from a microorganism such as *Rhodococcus rhodochrous* can be used to resolve (+/−)trans-7-phenyl-1-azabicyclo(4,2,0)-octan-8-one to L-ritalinic acid and the D-trans-7-phenyl-1-azabicyclo (4,2,0)-octan-8-one. This lactam is then hydrolyzed to the D-ritalinic acid by conventional means.

Trans-7-phenyl-1-azabicyclo(4,2,0)-octan-8-one may be prepared by the method of Corey, Mol, or Earle (Corey et al., *J. Amer. Chem. Soc.*, 87:2518 (1965); Earle et al., *J. Chem. Soc. C.*, 2093 (1969); Moll F. *Naturforsch.*, Teil B, 21:297 (1996).

Isolation of D-lactam

The reaction mixture prepared above is extracted with methylene chloride and the organic layer is dried with $MgSO_4$. The organic layer is then filtered and concentrated by rotary evaporation at 30° with reduced pressure, to yield an oil product. The oil product may be further purified by column chromatography.

Example 2

Preparation of D-threo-2-(piperid-2-yl)-2-phenylacetic acid from threo-2-(piperid-2-yl)-2-phenyl-2-acetamide Preparation of Amidase Amidase is obtained from *Acinetobacter baumanni* grown on 30 mM 2-cyanobutane as the sole carbon and nitrogen source in a minimal media. Fifty milliliters of Media A containing 30 mM 2-cyanobutane is inoculated with *Acinetobacter baumanni*. After the mixture in incubated at 30° C. for 48 hours, 10 ml of the mixture are subcultured into 250 ml of Media A with 30 mM 2-cyanobutane. After 40 hours of incubation at 30° C., the cells are concentrated to a paste by centrifugation at 10,000 G and washed with 50 ml phosphate buffer pH 7.5 and again concentrated to a paste by centrifugation at 10,000 G. The washed paste then is passed through a French Press at 17,000 psi to rupture the cells and produce cell extract. Cell debris is removed by centrifugation for one half hour at 100,000 G and the enzyme-containing supernatant collected.

Racemic threo-2-(piperid-2-yl)-2-phenyl-2-acetamide (0.5 g) prepared by, e.g. the method of Hartmann, U.S. Pat. No. 2,507,631, is added to a mixture of 20 ml of 50 mM potassium phosphate buffer pH 8 and 1 ml cell extract of amidase. The reaction is maintained at 30° C. until the enantiomer excess as determined by chiral chromatography is no less than 98% of D-ritalinic acid, generally about 5 hours under these conditions. An amidase with opposite stereoselectivity obtained from a microorganism such as *Rhodococcus rhodochrous* can be used to resolve DL-threo-2-(piperid-2-yl)-2-phenyl-acetamide to L-ritalinic acid and the D-threo-2-(piperid-2-yl)-2-phenyl-acetamide. This amide is then hydrolyzed to the D-ritalinic acid by conventional means.

Example 3

Preparation of D-threo-2-(piperid-2-yl)-2-phenyl acetic acid from trans-7-phenyl-1-azabicyclo(4,2,0)-octan-8-one Racemic trans-7-phenyl-1-azabicyclo(4,2,0)-octan-8-one (0.5 g) is added to a mixture of 20 ml 50 mM phosphate buffer pH 7.5 and 1 ml of *Pseudomonas putida* cell extract. The reaction is maintained at 30° C. until the enantiomeric excess as determined by chiral chromatography is no less than 98% D-ritalinic acid, generally about 24 hours under these conditions. Alternatively, a cell extract containing an amidase of opposite stereoselectivity may be used to effect a resolution of racemic trans-7-phenyl-1-azabicyclo (4,2,0)-octan-8-one where L-ritalinic acid is produced and the D-lactamis isolated as the product.

Isolation of D-lactam

The reaction mixture prepared above is extracted with methylene chloride and the organic layer dried with $MgSO_4$. The organic layer is then filtered and concentration by rotary evaporation at 30° with reduced pressure, to yield an oil. The oil product may be further purified by column chromatography.

Example 4

Preparation of D-threo-2-(piperid-2-yl)-2-phenyl-acetic acid from threo-2-(piperid-2-yl)-2-phenyl-acetonitrile Nitrile hydratase and amidase are obtained from *Alcaligenes faecalis* grown on 30 mM 2-cyanobutane or 2-phenylacetonitrile as the sole carbon and nitrogen source in a minimal media. Fifty milliliters of Media A containing 30 mM 2-cyanobutane is inoculated with *Alcaligenes faecalis*. After the mixture is incubated at 30° C. for 48 hours, 10 ml of the mixture are subcultured into 250 ml of Media A with 30 mM 2-cyanobutane or 2-phenylacetonitrile. After 40 hours of incubation at 30° C., the cells are concentrated a paste by centrifugation at 10,000 G and washed with 50 ml phosphate buffer pH 7.5 and again concentrated to a paste by centrifugation at 10,000 G. The washed paste then is passed through a French Press at 17,000 psi to rupture the cells and produce cell extract. Cell debris is removed by centrifugation for one half hour at 100,000 G and the enzyme-containing supernatant collected.

Racemic threo-2-(piperid-2-yl)-2-phenyl-2-acetonitrile (0.5 g) is added to a mixture of 20 ml of 50 mM potassium phosphate buffer pH 8 and 1 ml cell extract of *Alcaligenes faecalis* with nitrile hydratase and amidase activity. The reaction is maintained at 30° C. until the enantiomer excess as determined by chiral chromatography is no less than 98% of D-ritalinic acid, generally about 5 hours under these conditions.

Example 5

The Use of an Esterase/lipase for the Stereoselective Enrichment of DL-threo-α-phenyl-α-piperidyl-acetic acid methyl ester A microbial source of a stereoselective esterase or lipase may be obtained from commercial sources such as Novo Nordisk's "Humicola lipolase" or an ATCC Pseudomonas strain 31809 or 31808. Esterase/lipase is obtained from Pseudomonas sp. ATCC strain 31809 grown on 1% olive oil in media A supplemented with 8 g/l nutrient broth. Fifty ml of media A containing the 1% olive oil and 8 g/l nutrient broth is inoculated with Pseudomonas sp. ATCC strain 31809. After the mixture is incubated at 30° C. for 48 hours, 10 ml of the mixture are subcultured into 250 ml of media with 1% olive oil supplemented with 8 g/l nutrient broth. After 24 hours of incubation at 30° C., the cells are concentrated to a paste by centrifugation at 10,000 G and washed with 50 ml phosphate buffer, pH 7.5 and again concentrated to a paste. Cells are ruptured as above.

DL-threo-α-phenyl-α-piperidylacetic acid methyl ester (0.5 g) prepared by the method of Hartmann is added to a mixture of 20 ml of 50 mM potassium phosphate buffer pH and 1 ml cell extract. The reaction is maintained at 30° C. until the enantiomeric excess, as determined by chiral chromatography, is no less than 98% D-threo-methylphenidate, generally in about 25 hours under these conditions.

Preparation of Exemplary Dosage Forms

Example 6

Tablets for chewing, each containing 5 milligrams of D-threo-methylphenidate, can be prepared in the following manner:

Composition (for 1000 tablets)

| | |
|---|---|
| D-threo-methylphenidate | 5.00 grams |
| mannitol | 15.33 grams |
| lactose | 10.00 grams |
| talc | 1.40 grams |
| glycine | 0.83 grams |
| stearic acid | 0.66 grams |
| saccharin | 0.10 grams |
| 5% gelatin solution q.s. | |

The solid ingredients are each forced through a 0.25 mm mesh sieve. The mannitol and the lactose are mixed, granulated with the addition of gelatin solution, forced through a 2 mm mesh sieve, dried at 50° C. and forced through a 1.7 mm mesh sieve. The D-threo-methylphenidate, glycine and saccharin are carefully mixed, the granulated mannitol and lactose, stearic acid and talc added and the whole mixed thoroughly. The mass is compressed to form tablets of approximately 5 mm diameter which are concave on both sides and have a breaking groove on the one side.

Example 7

Tablets, each containing 10 milligrams of D-threo-methylphenidate, can be prepared in the following manner:
composition (for 1000 tablets)

| | |
|---|---|
| D-threo-methylphenidate | 10.0 grams |
| lactose | 328.5 grams |
| corn starch | 17.5 grams |
| polyethylene glycol 6000 | 5.0 grams |
| talc | 25.0 grams |
| magnesium stearate | 4.0 grams |
| demineralized water q.s. | |

The solid ingredients are first forced through a 0.6 mm mesh sieve. Then the d-threo-methylphenidate, lactose, talc, magnesium stearate and half of the starch are intimately mixed. The other half of the starch is suspended in 65 milliliters of water and this suspension is added to a boiling solution of the polyethylene glycol in 260 milliliters of water. The resulting paste is added to the pulverulent substances, and the whole is mixed and granulated, if necessary with the addition of water. The granulate is dried overnight at 35° C., forced through a sieve of 1.2 mm mesh and compressed to form tablets of approximately 5 mm diameter which are concave on both sides and have a breaking notch on the upper side.

Example 8

Gelatin dry-filled capsules, each containing 20 milligrams of D-threo-methylphenidate, can be prepared in the following manner:
Composition (for 1000 capsules)

| | |
|---|---|
| D-threo-methylphenidate | 20.0 grams |
| microcrystalline cellulose | 6.0 grams |
| sodium lauryl sulfate | 0.4 grams |
| magnesium stearate | 1.6 grams |

The sodium lauryl sulfate is sieved into the D-threo-methylphenidate through a 0.2 mm mesh sieve and the two components intimately mixed for 10 minutes. The microcrystalline cellulose is then added through a 0.9 mm mesh sieve and the whole again intimately mixed for 10 minutes. Finally, the magnesium stearate is added through a 0.8 mm mesh sieve and, after mixing for a further 3 minutes, the mixture is introduced in portions of 28 milligrams each into gelatin dry-fill capsules.

Example 9

A 0.2% injectable or infusible solution can be prepared, in the following exemplary manner:

| | |
|---|---|
| D-threo-methylphenidate | 5.0 grams |
| sodium chloride | 22.5 grams |
| phosphate buffer pH 7.4 | 300.0 grams |
| demineralized water to 2500 ml. | |

The D-threo-methylphenidate is dissolved in 1000 milliliters of water and filtered through a microfilter or slurried in 1000 ml of $H_2O$. The buffer solution is added and the whole is made up to 2500 milliliters with water. To prepare unit dosage forms, portions of 1.0 or 2.5 milliliters each are introduced into glass ampoules such that each contains, respectively 2.0 or 5.0 milligrams of D-threo-methylphenidate.

What is claimed is:

1. A pharmaceutical unit dosage comprising from about 1 to about 50 milligrams of compound having the formula:

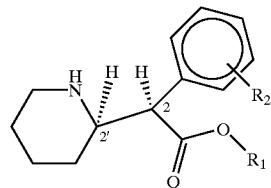

or a pharmaceutically acceptable salt thereof, wherein $R_1$ is $C_1$–$C_4$ alkyl, and $R_2$ is hydrogen or $C_1$–$C_4$ alkyl, in a pharmaceutically acceptable carrier or diluent, said dosage form having less than 10% by weight of other stereoisomers of the compound or salt.

2. The unit dosage of claim 1 comprising from about 2 to about 20 milligrams of said compound.

3. The unit dosage of claim 1 comprising from about 2½ to about 12 milligrams of said compound.

4. The unit dosage of claim 1 in a form suitable for oral administration.

* * * * *

UNITED STATES PATENT AND TRADEMARK OFFICE
CERTIFICATE OF CORRECTION

PATENT NO. : 6,528,530 B2
DATED : March 4, 2003
INVENTOR(S) : Andrew L. Zeitlin and Maghsoud M. Dariani It is certified that error appears in the above-identified patent and that said Letters Patent is hereby corrected as shown below:

Title page,
Item [56], References Cited, OTHER PUBLICATIONS, "Patrick et al.," reference, delete "thre-o-Methylphenidate", and insert -- threo-Methylphenidate", --; "Srinivas et al.," reference, delete "dl-th-reo-Methylphenidate" and insert -- dl-threo-Methylphenidate --;

Column 1,
Line 29, delete "Nervcus" and insert -- Nervous --;
Line 32, delete "Graenhill," and insert -- Greenhill, --;

Column 4,
Line 16, delete "Lerythro," and insert -- L erythro, --;

Column 5,
Line 21, delete "substituients" and insert -- substituents --;

Column 7,
Line 20, delete "(+/- -)" and insert -- (+/-) --;

Column 8,
Line 29, delete "D-lactamis" and insert -- D-lactam is --;
Line 52, after "concentrated" insert -- to --;

Column 9,
Lines 26-27, delete "buffer pH and 1 ml" and insert -- buffer pH 7 and 1 ml --.

Signed and Sealed this

Twenty-eighth Day of September, 2004

JON W. DUDAS
*Director of the United States Patent and Trademark Office*